United States Patent [19]

Lowther et al.

[11] Patent Number: 5,739,167
[45] Date of Patent: Apr. 14, 1998

[54] DESFERRIOXAMINE-B SALTS AND THEIR USE AS ORALLY EFFECTIVE IRON CHELATORS

[75] Inventors: Nicholas Lowther; Ian Francis Hassan; Ian Timothy William Matthews, all of Horsham, England

[73] Assignee: Novartis Corporation, Summit, N.J.

[21] Appl. No.: 343,599

[22] PCT Filed: May 6, 1993

[86] PCT No.: PCT/GB93/00940

§ 371 Date: Nov. 30, 1994

§ 102(e) Date: Nov. 30, 1994

[87] PCT Pub. No.: WO93/24451

PCT Pub. Date: Dec. 9, 1993

[30] Foreign Application Priority Data

Jun. 3, 1992 [GB] United Kingdom ............... 9211779

[51] Int. Cl.⁶ ........................................ A01N 37/18
[52] U.S. Cl. ................... 514/616; 562/623; 564/191; 564/193; 564/197
[58] Field of Search ............... 514/616; 562/623; 564/191, 193, 197

[56] References Cited

U.S. PATENT DOCUMENTS

| | | | |
|---|---|---|---|
| 3,247,197 | 4/1966 | Gaeumann | 562/623 |
| 3,652,411 | 3/1972 | Commichau | 508/282 |
| 3,679,660 | 7/1972 | Magnus | 536/54 |
| 5,185,368 | 2/1993 | Peter et al. | 514/476 |

FOREIGN PATENT DOCUMENTS 0162324  11/1985  European Pat. Off. .
8503290  8/1985  WIPO .

OTHER PUBLICATIONS

Calendar et al "Iron chelating with oral desferrioxamine" Chem Abs. #94:58388q vol. 96, No. 9 Mar. 1981.
Lancet vol. 2, No. 816q, 1980 p. 689.

*Primary Examiner*—Paul F. Shaver
*Attorney, Agent, or Firm*—Marla J. Mathias; Norbert Gruenfeld; Gregory D. Ferraro

[57] ABSTRACT

A salt of formula (I) where X denotes a group of formula (II), Y denotes a group of formula (III) and R denotes the residue of an aliphatic or cycloaliphatic sulphonic acid having at least 3 carbon atoms after removal of an —SO₃H group therefrom.

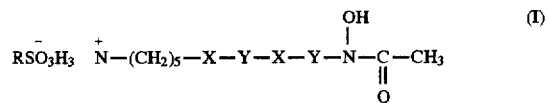

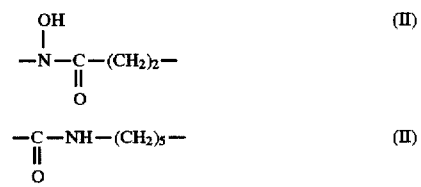

16 Claims, No Drawings

DESFERRIOXAMINE-B SALTS AND THEIR USE AS ORALLY EFFECTIVE IRON CHELATORS

This is a 371 of PCT/GB 93/00940, filed May 6, 1993.

This invention relates to salts of desferrioxamine-B, and to pharmaceutical compositions containing such salts as active ingredients.

The preparations of desferrioxamine-B and pharmaceutically acceptable addition salts thereof are described in U.S. Pat. No. 3,247,197. The amine and salts thereof such as those described in the above mentioned U.S. patent exhibit a marked ability to form stable complexes with trivalent metal ions, especially $Fe^{3+}$. Consequently, desferrioxamine-B (as the methanesulphonate salt) is of immense importance as a pharmacological iron-chelator in the treatment of iron-overload diseases such as beta-thalassemia. As the only currently marketed drug which is available for the treatment of thalassemia, desferrioxamine-B is vital to the survival of patients suffering from this disease.

Administration of desferrioxamine-B (as the methane sulphonate salt) via slow (8 to 12 hour) subcutaneous infusion is now widely accepted as the route necessary to control transfusional iron overload in beta-thalassemics. However, such a mode of treatment is laborious, uncomfortable and inconvenient for the patient, and involves high costs. Patient compliance is poor: non-compliance with iron-chelation therapy has been suspected to be the most important cause of death amongst British thalassemics. Hence there is a great need for simpler, more convenient and cheaper iron-chelation therapy, criteria which would be met via an oral dosage form.

This need has been apparent for a long time, and numerous attempts have been made over many years to obtain a form of desferrioxamine-B which is effective in iron-overload therapy when administered orally. Such attempts have included formulations based on the methanesulphonate salt, other known salts and other derivatives. All of these attempts have proved unsuccessful.

It has now been found, in accordance with the present invention, that novel salts of desferrioxamine-B having enhanced lipophilicity provide a means of improving the clinical efficiency of the drug to such an extent that it is effective when administered orally. These salts can exhibit unexpectedly high lipophilicity under physiological conditions, whilst at the same time having good stability and effective iron-chelating properties.

Accordingly, the present invention provides, in one aspect, a salt of formula

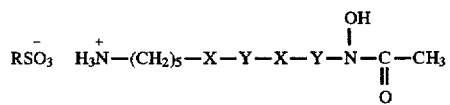

where X denotes a group of formula

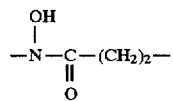

Y denotes a group of formula

and R denotes the residue of an aliphatic or cycloaliphatic sulphonic acid having at least three carbon atoms after removal of a —$SO_3H$ group therefrom.

R may contain up to 30 carbon atoms. Preferably it contains at least 6 carbon atoms, more preferably 6 to 20 carbon atoms, especially 6 to 12 carbon atoms, more especially 8 to 12 carbon atoms, most especially 8 to 10 carbon atoms. R may be, for example, a hydrocarbyl group, i.e. the residue after removal of the —$SO_3H$ group from an alphatic or cycloaliphatic hydrocarbyl sulphonic acid, for example an alkanesulphonic, cycloalkanesulphonic, alkenesulphonic or alkynesulphonic acid such as propane-1-sulphonic acid, propane-2-sulphonic acid, butane-1-sulphonic acid, 2-methyl-1-propanesulphonic acid, pentane-1-sulphonic acid, 3-methyl-1-butanesulphonic acid, 2-methyl-1-butanesulphonic acid, pentane-2-sulphonic acid, hexane-1-sulphonic acid, 2-ethyl-butanesulphonic acid, 4-methyl-2-pentanesulphonic acid, hexane-2-sulphonic acid, heptane-1-sulphonic acid, heptane-2-sulphonic acid, octane-1-sulphonic acid, octane-2-sulphonic acid, nonane-1-sulphonic acid, nonane-2-sulphonic acid, decane-1-sulphonic acid, dodecane-1-sulphonic acid, tetradecane-1-sulphonic acid, hexadecane-1-sulphonic acid, octadecane-1-sulphonic acid, cyclopentanesulphonic acid, cyclohexane sulphonic acid, allylsulphonic acid, 2-methyl-2-propene-1-sulphonic acid, hexene-1-sulphonic acid, octene-1-sulphonic acid, decene-1-sulphonic acid, dodecene-1-sulphonic acid, tetradecene-1-sulphonic acid, hexadecene-1-sulphonic acid, cyclopentene-1-sulphonic acid, cyclohexene-1-sulphonic acid, 1,3-cyclohexadiene-1-sulphonic acid, methylacetylene sulphonic acid or decylacetylene sulphonic acid.

In other embodiments of the invention, R may be a substituted hydrocarbyl, usually substituted alkyl group, i.e. the residue, after removal of a $SO_3H$ group, of a substituted hydrocarbyl sulphonic acid, for example a hydroxy-, alkoxy-, acyloxy-, alkoxycarbonyl-, halogen- or amino-substituted alkylsulphonic acid such as 2-hydroxypropane-1-sulphonic acid, 3-hydroxypropane-1-sulphonic acid, 1-hydroxyoctane-2-sulphonic acid, 2-ethoxyethane-1-sulphonic acid, 2-acetoxy-1-butanesulphonic acid, dioctyl sulphosuccinate, 3-chloropropane-1-sulphonic acid, 4-bromobutane-1-sulphonic acid, 1-aminopropane-2-sulphonic acid, 3-aminopropane-1-sulphonic acid, 2-aminopropane-1-sulphonic acid, 1-aminobutane-2-sulphonic acid, 4-aminobutane-1-sulphonic acid or 2-aminobutane-1-sulphonic acid.

Preferably R is the residue of a hydrocarbyl sulphonic acid, especially of an alkanesulphonic acid, after removal of a —$SO_3H$ group therefrom. In specific especially preferred embodiments, R is the residue, after removal of a —$SO_3H$ group, of hexane-1-sulphonic acid, octane-1-sulphonic acid, decane-1-sulphonic acid or dodecane-1-sulphonic acid.

Salts of formula I can be prepared by reacting desferrioxamine-B, i.e. a compound of formula

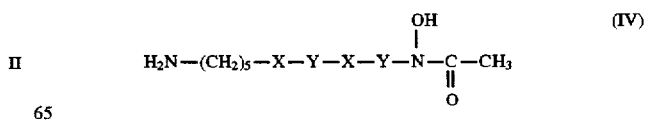

where X and Y are as hereinbefore defined, with a sulphonic acid of formula $RSO_3H$ where R is as hereinbefore defined.

or a salt-forming derivative thereof such as a sulphonyl halide, generally using conventional reaction procedures. The salt-forming reaction is conveniently carried out by reacting desferrioxamine-B with a free acid of formula $RSO_3H$ in aqueous methanol, the salt which crystallises being purified by recrystallisation from aqueous methanol or a mixture of water, methanol and acetone. Desferrioxamine-B may be prepared as described in U.S. Pat. No. 3,247,197 or U.S. Pat. No. 3,153,621.

It has been found that by mixing a salt of the invention as hereinbefore described with another water-soluble salt of a sulphonic acid of formula $RSO_3H$ where R is as hereinbefore defined, a further enhancement of lipophilicity can be achieved. The further water-soluble salt is preferably an alkali metal salt, especially a potassium or sodium salt. This further salt may be used in pharmaceutical compositions in an amount not exceeding its critical micellar concentration. For example, it may be used in an amount up to 50%, such as 0.1 to 50%, by weight of the salt of the invention.

It has also been found that a mixture of desferrioxamine-B methanesulphonate together with a water-soluble salt of a sulphonic acid of formula $RSO_3H$ where R is as hereinbefore defined, which is believed to form a salt of desferrioxamine-B with the acid of formula $RSO_3H$, i.e. a salt of the invention, under physiological conditions, also exhibits enhanced lipophilicity. The salt of the acid of formula $RSO_3H$ is preferably an alkali metal salt, especially a potassium or sodium salt. This salt may be used in pharmaceutical compositions to provide, together with desferrioxamine-B methanesulphonate, a precursor for a salt of the invention, in an amount not exceeding its critical micellar concentration. For example, it may be used in an amount up to 50%, such as 0.1 to 50% by weight of the desferrioxamine-B methanesulphonate.

The present invention also provides pharmaceutical compositions containing as active ingredient a salt of the invention as hereinbefore described, or a precursor therefor comprising a mixture of desferrioxamine-B methanesulphonate and a water-soluble salt of an acid of formula $RSO_3H$ where R is as hereinbefore defined. Where the composition contains a preformed salt of the invention, the salt may be used in admixture with another water-soluble salt of an acid of formula $RSO_3H$ as hereinbefore described.

Preferred pharmaceutical compositions are those suitable for enteral, especially oral, administration to warm-blooded animals. Daily dosages may be up to about 4 g, for example 500 mg to 4 g. The compositions may contain the active ingredient alone or in combination with a pharmaceutically acceptable excipient. The compositions may be in dosage unit forms such as tablets, coated tablets, hard or soft gelatin capsules or syrups. These can be prepared using known procedures, for example by conventional mixing, granulating, tablet coating, dissolving or lyophilising processes. Thus, pharmaceutical compositions for oral administration can be obtained by combining the active ingredient with solid carriers, optionally granulating the resulting mixture, and processing the mixture or granulate, if desired or necessary after the addition of suitable excipients, to give tablets or coated tablet cores.

Suitable excipients are, in particular, fillers, such as sugars, for example lactose, sucrose, mannitol or sorbitol, cellulose preparations and/or calcium phosphates, for example tricalcium phosphate or calcium hydrogen phosphate, and binders, such as starches for example, corn, wheat, rice or potato starch, gelatin, tragacanth, methylcellulose and/or polyvinylpyrrolidone, and/or, if desired, distintegrants, such as the abovementioned starches, and also carboxymethyl starch, cross-linked polyvinylpyrrolidone, agar, alginic acid or a salt thereof such as sodium alginate, and/or flow regulators and lubricants, for example silica, talc, stearic acid or salts thereof such as magnesium stearate or calcium stearate, and/or polyethylene glycol. Coated tablet cores can be provided with suitable coatings, which if appropriate are resistant to gastric juices, using, inter alia, concentrated sugar solutions which may contain gum arabic, talc, polyvinylpyrrolidone, polyethylene glycol and/or titanium dioxide, shellac solutions in suitable organic solvents or solvent mixtures or, for the preparation of coatings resistant to gastric juices, solutions of suitable cellulose preparations such as acetylcellulose phthalate or hydroxypropylmethylcellulose phthlate. Dyes or pigments can be added to the tablets or coated tablets, for example to identify or indicate different doses of active ingredient.

Other pharmaceutical preparations suitable for oral administration are hard gelatin capsules and also soft sealed capsules made from gelatin and a plasticizer such as glycerol or sorbitol. The hard capsules can contain the active ingredient in the form of granules, for example in admixture with fillers such as lactose, binders such as starches, and/or lubricants such as talc or magnesium stearate, and if desired, stabilizers. In soft capsules, the active ingredient is preferably dissolved or suspended in a suitable liquid, such as a fatty oil, paraffin oil or a liquid polyethylene glycol, to which a stabiliser can be added.

Salts of formula I in which R contains 8 or more carbon atoms have very low intrinsic dissolution rates in aqueous media, indicating their suitability for the formulation of long acting depot, or other sustained release, dosage forms of desferrioxamine-B.

The present invention also provides pharmaceutically acceptable salts of formula I as hereinbefore described, or precursors therefor as hereinbefore described, for use in a therapeutic method of treating a warm blooded animal body, for the treatment of indications such as aluminium overload, Alzheimer's disease, malaria, reperfusion injury, cancer and particularly in the treatment of iron-overload diseases. The present invention further provides the use of such salts or precursors for the preparation of a pharmaceutical composition for the treatment of the abovementioned indications, particularly iron-overload diseases.

The invention is illustrated by the following Examples, in which parts and percentages are by weight, unless otherwise indicated.

EXAMPLE 1

A solution of decane-1-sulphonic acid, sodium salt (1.00 g, 4.09 mmol) in water (100 ml) is passed down a column of AG50WX2 cation exchange resin available from Bio-rad ($H^+$ form, 50 ml). The column is washed with water (100 ml). The combined eluant is concentrated to 25 ml under reduced pressure. The concentrate is added, with stirring, at ambient temperature to a solution of desferrioxamine-B free base (2.24 g, 3.99 mmol) in 60/40 v/v methanol/water (250 ml). The reaction mixture is allowed to stand at ambient temperature for 8 hours. The mixture is concentrated under reduced pressure to 50 ml, at which point a white solid crystallises. This is collected by filtration, recrystallised from aqueous methanol and dried under reduced pressure to yield 1.39 g (44%) of the decane-1-sulphonate/salt of desferrioxamine-B. Mp 149° C., $C_{35}H_{70}O_{11}N_6S$ Calcd C:53.69%, H:9.01%, N:10.73%, S:4.09%; Found C:53.51%, H:9.01%, N:10.73%, S:4.08%. The homogeneity of the product is confirmed by differential scanning calorimetry (under nitrogen, scan rate 5° C./min, single endotherm at 149° C. corresponding to the melting point of the product).

and by hplc under the following conditions:- Column: Novapak ODS RCM cartridge available from Waters; Mobile phase: A-Phosphate buffer, pH7.0 containing 4 mM nitrilotriacetic acid (NTA), B- 50/50 v/v mixture of buffer A and acetonitrile; Flow rate: 1 ml/min; Gradient (Mins/% buffer A): 0/95 20/60 21/60 25/95; Detection: uv/vis at 215 nm and 440 nm; RT: 20.5 min.

EXAMPLE 2

Following a procedure analogous to that of Example 1, butane-1-sulphonic acid and desferrioxamine-B are reacted to give the butane-1-sulphonate salt of desferrioxamine-B. Mp 134° C. $C_{29}H_{58}O_{11}N_6S$ Calcd. C: 49.84%, H: 8.36%, N:12.03%, S:4.59%; Found C:49.52%, H:8.19%, N:12.00%, S:4.14%.

EXAMPLE 3

Following a procedure analogous to that of Example 1, hexane-1-sulphonic acid and desferrioxamine-B are reacted to give the hexane-1-sulphonate salt of desferrioxamine-B. Mp 138° C. $C_{31}H_{62}O_{11}N_6S$ Calcd C: 51.22%, H:8.60%, N:11.56%, S:4.41%; Found C: 51.04%, H: 8.50%, N:11.40%, S:4.19%.

EXAMPLE 4

Following a procedure analogous to that of Example 1, octane-1-sulphonic acid and desferrioxamine-B are reacted to give the octane-1-sulphonate salt of desferrioxamine-B. Mp 144° C. $C_{33}H_{66}O_{11}N_6S$ Calcd C: 52.50%, H:8.81%, N:11.13%, S:4.25%; Found C: 52.43%, H:8.75%, N:11.16%, S:4.18%.

EXAMPLE 5

Following a procedure analogous to that of Example 1, dodecane-1-sulphonic acid and desferrioxamine-B are reacted to give the dodecane-1-sulphonate salt of desferrioxamine-B. Mp 151° C. $C_{37}H_{74}O_{11}N_6S$ Calcd C: 54.79%, H:9.20%, N:10.36%, S:3.95%; Found C: 54.74%, H: 9.15%, N:10.21%, S: 4.07%.

EXAMPLES 6–10

The partition coefficients of the salts prepared in Examples 1 to 5 between n-octanol and water are determined by the 'shake-flask' method of Leo et al, Chem. Rev., 71(6), 525 (1971).

The n-octanol and aqueous phases are mutually saturated prior to conducting the experiment. The desferrioxamine-B sulphonic acid addition salt is dissolved in the aqueous phase at a concentration of 0.005 mol/l and the partition experiment is performed by shaking the vessel containing the two phases until an equilibrium has been achieved. Experiments have revealed that such an equilibrium is set up within 30 minutes shaking—no change in observed partition coefficient is observed if shaking is continued up to 24 hours. After equilibrium has been achieved, the sample is centrifuged to enable phase separation. Both organic and aqueous phases are analysed for desferrioxamine-B content via extraction of an appropriate aliquot, quenching with an aqueous (for assay of the aqueous phase) or methanolic (for assay of the n-octanol phase) solution of $FeCl_3$, and measurement of the absorption of the characteristic ferrioxamine-B chelate at ca. 450 nm. Respective calibration plots (absorbance vs. concentration of desferrioxamine-B sulphonic acid salt) for the assay of both aqueous and organic phases show a linear response over the concentration range studied. The results obtained are as follows:

| Example | Salt | Partition Coefficient |
|---|---|---|
| 6 | butanesulphonate | 0.008 |
| 7 | hexanesulphonate | 0.020 |
| 8 | octanesulphonate | 0.121 |
| 9 | decanesulphonate | 0.366 |
| 10 | dodecanesulphonate | 0.450 |

EXAMPLES 11–15

The partition coefficients of the salts prepared in Examples 1 to 5 between n-octanol and an aqueous phosphate buffer at pH7.4 having an ionic strength of 0.31 mol/l are determined using the procedure of Examples 6–10. The results obtained are as follows:

| Example | Salt | Partition Coefficient |
|---|---|---|
| 11 | butanesulphonate | 0.006 |
| 12 | hexanesulphonate | 0.010 |
| 13 | octanesulphonate | 0.047 |
| 14 | decanesulphonate | 0.060 |
| 15 | dodecanesulphonate | 0.028 |

The use of n-octanol/aqueous media partition coefficients as a model for the lipophilicity of drugs is well established (see the abovementioned Leo et al reference). The aqueous phase in Examples 11 to 15 simulates physiological conditions. The results show surprisingly high partition coefficients for salts of the invention in such conditions.

EXAMPLES 16–17

Tablets are prepared from the salts of Examples 1 and 4 by compressing a mixture of 99 parts of the salt and 1 part of magnesium stearate in a 13 mm die for 2 minutes under a pressure of $4 \times 10^5$ kPa. The intrinsic dissolution rates of the tablets are determined using a Langenbucher flow-through apparatus, with water at 25° C. as the dissolution medium. The amount of desferrioxamine-B dissolved in the medium is measured at intervals using a spectrophotometric assay at 215 nm. The results obtained are as follows:

| Time (min) | % Desferrioxamine-B salt dissolved | |
|---|---|---|
| | Ex. 16 (decanesulphonate) | Ex. 17 (octanesulphonate) |
| 1 | 1.01 | 1.71 |
| 2 | 1.65 | 3.07 |
| 5 | 2.90 | 6.88 |
| 10 | 4.67 | 10.56 |
| 15 | 6.17 | 14.22 |
| 20 | 7.50 | 17.94 |
| 30 | 9.97 | 24.73 |
| 50 | 14.21 | 37.09 |
| 75 | 18.80 | 48.75 |
| 100 | 22.92 | 58.34 |
| 125 | 26.62 | 66.38 |
| 150 | 30.13 | 72.38 |
| 175 | 33.49 | 79.13 |
| 200 | 36.85 | 84.91 |
| 225 | 39.97 | 89.25 |
| 250 | 42.94 | 92.50 |
| 275 | 45.87 | 94.91 |
| 300 | 48.81 | 96.34 |

These results show that the intrinsic rate of release of the octanesulphonate and decanesulphonate salts into the aqueous dissolution medium is slow. This can be exploited in the formulation of long-acting depot, or other sustained release dosage forms of desferrioxamine-B.

EXAMPLES 18–19

The iron-chelating properties of salts of the invention in a biological system are determined by means of a bioassay in which the growth inhibiting effect of the salts on cells through iron removal is measured by the uptake of radio-actively labelled thymidine into the cells. The bioassay is carried out using a Daudi cell line (B-cell lymphoma), a Roswell Park Memorial Institute (RPMI) 1640 medium containing 1 µM ferric citrate and supplements as low iron washing medium and RPMI 1640 together with 5% by weight of foetal calf serum as passaging medium.

The cells are fed 24 hours before use. They are washed twice in the low iron washing medium to remove any excess iron and diluted with this medium to a concentration of $0.2 \times 10^6$ cells/0.180 ml. To 0.180 ml aliquots are added 0.02 ml of solutions of the desferrioxamine-B salts under test in phosphate-buffered saline (PBS) to give concentrations ranging from a Control containing no salt to a 20 µM solution. The cells are then incubated at 37° C. in an atmosphere containing 5% by volume of carbon dioxide for 72 hours, being pulsed for the last 8 hours of that time with labelled [$^3$H] Thymidine at 5 micro Ci/ml. The resulting cells are harvested and their radioactive disintegrations are counted for 10 minutes. The results are shown in the table below as the average of 4 separate experiments (except the Control result in Example 18 which is the average of 3 separate experiments).

| Concentration of Salt (µM) | Disintegrations Per Minute | |
|---|---|---|
| | Ex 18-octanesulphonate | Ex 19-decanesulphonate |
| 20 | 482 | 494 |
| 15 | 1065 | 1101 |
| 10 | 2292 | 2172 |
| 7.5 | 3716 | 3262 |
| 6 | 4122 | 4382 |
| 5 | 5373 | 5139 |
| 4 | 6280 | 5445 |
| 3 | 7109 | 6599 |
| 2 | 7651 | 6847 |
| 1 | 14765 | 14161 |
| 0.5 | 21830 | 23603 |
| 0 | 22297 | 23897 |

These results show that as the concentration of the salts of the invention is increased, cell growth is reduced due to removal of iron, thus indicating that the salts of the invention have effective iron-chelating properties in biological systems.

EXAMPLE 20

The salt of Example 4 (400 parts) is mixed with polyvinylpyrrolidone (8 parts) and sodium lauryl sulphate (3 parts). Sufficient water is incorporated into the mixture to give a cohesive mass, which is passed through a nylon sieve and then dried at 50° C. for 3 to 4 hours. The dried mass is received and the resulting granules are used to fill size 00 gelatin capsules, each capsule containing 400 mg of the salt of Example 4. The filled capsules are coated with a primer coat of a mixture of hydroxylpropyl methylcellulose (10 parts), purified talc (9 parts), Cremophor RH 40 —a solubilising agent available from BASF (0.8 parts), FD & C Red No. 3 vegetable dye (0.2 parts) and purified water (80 parts). The primer coated capsules are coated, using a fluidised bed apparatus, with an enteric coating of a mixture of Eudragit L30D—an anionic polymer available from Dumas Chemicals (32.15 parts), a polyethylene glycol having a molecular weight of 8000 (1.44 parts), purified talc (1.04 parts), a silicone antifoam emulsion (0.08 parts), ammonia solution (0.05 parts) and purified water (65.24 parts). The resulting enteric-coated capsules are suitable for oral administration.

EXAMPLE 21

The partition coefficients of the salt prepared in Example 4 and mixtures thereof with sodium octane-1-sulphonate between n-octanol and water are determined using the procedure of Examples 6–10. The salt of Example 4 is dissolved in water at a concentration of 4.5 mg/ml. For the mixtures, the sodium salt is mixed with the salt of Example 4 and the mixture is dissolved in the water at 50° C. The results obtained are as follows:

| % Sodium Salt by weight of Salt of Example 4 | Partition Coefficient |
|---|---|
| 0 | 0.121 |
| 10 | 0.167 |
| 20 | 0.198 |
| 30 | 0.231 |
| 40 | 0.279 |
| 50 | 0.294 |

EXAMPLE 22

Example 21 is repeated using the salt of Example 1 in place of the salt of Example 4, and the sodium salt of decane-1-sulphonic acid in place of sodium octane-1-sulphonate. The results obtained are as follows:

| % Sodium Salt by weight of Salt of Example 1 | Partition Coefficient |
|---|---|
| 0 | 0.366 |
| 10 | 0.762 |
| 20 | 0.838 |
| 30 | 1.369 |
| 40 | 1.420 |
| 50 | 1.877 |

EXAMPLE 23

The partition coefficients of desferrioxamine-B methanesulphonate and mixtures thereof with sodium decane-1-sulphonate between n-octanol and water are determined using the procedure of Examples 6–10. The methanesulphonate is used at a concentration of 6.0 mg/ml in the water. For the mixtures, the sodium salt is mixed with the methanesulphonate and the mixture is dissolved in the water at 50° C. The results obtained are as follows:

| % Sodium Decanesulphonate by weight of Desferrioxamine-B Methanesulphonate | Partition Coefficient |
|---|---|
| 0 | 0.002 |
| 10 | 0.110 |
| 20 | 0.373 |
| 30 | 0.662 |
| 40 | 0.812 |
| 50 | 1.182 |

EXAMPLE 24

Example 23 is repeated, replacing the sodium decane-1-sulphonate used in that Example by sodium octane-1-sulphonate. The results obtained are as follows:

| % Sodium Octanesulphonate by weight of Desferrioxamine-B Methanesulphonate | Partition Coefficient |
|---|---|
| 0 | 0.002 |
| 10 | 0.049 |
| 20 | 0.102 |
| 30 | 0.153 |
| 40 | 0.196 |
| 50 | 0.250 |

We claim:

1. A salt of formula

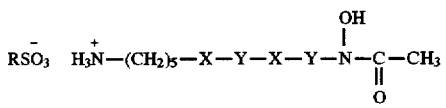

where X denotes a group of formula

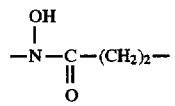

Y denotes a group of formula

and R denotes the residue of an aliphatic or cycloaliphatic sulphonic acid having from 6 to 20 carbon atoms after removal of a —SO$_3$H group therefrom.

2. A salt according to claim 1, in which R has 6 to 12 carbon atoms.

3. A salt according to claim 1, in which R has 8 to 10 carbon atoms.

4. A salt according to claim 1 in which R is the residue of a hydrocarbyl sulphonic acid after removal of a —SO$_3$H group therefrom.

5. A salt according to claim 4, in which the sulphonic acid is an alkanesulphonic acid.

6. A salt according to claim 5, in which the sulphonic acid is hexane-1-sulphonic acid, octane-1-sulphonic acid, decane-1-sulphonic acid or dodecane-1-sulphonic acid.

7. A salt of formula I according to claim 1 in admixture with a further water-soluble salt of a sulphonic acid of formula RSO$_3$H, where R is the residue of an aliphatic or cycloaliphatic sulphonic acid having from 6 to 20 carbon atoms after removal of a —SO$_3$H group therefrom.

8. A salt according to claim 7, in which the further salt is an alkali metal salt.

9. A salt according to claim 7, in which the further salt is present in an amount up to 50% by weight of the salt of formula I.

10. A pharmaceutical composition containing as active ingredient a salt according to claim 1 or a mixture of desferrioxamine-B methanesulphonate with a water-soluble salt of an acid of formula RSO$_3$H where R is as defined in claim 1.

11. A composition according to claim 10, in which said water-soluble salt is an alkali metal salt.

12. A composition according to claim 10, in which said water-soluble salt is present in an amount up to 50% by weight of the desferrioxamine-B methanesulphonate.

13. A composition according to claim 10, for oral administration.

14. A composition according to claim 10 which also contains a pharmaceutically acceptable excipient.

15. A process for the preparation of a salt according to claim 1 which comprises reacting desferrioxamine-B with an acid of formula RSO$_3$H, where R denotes the residue of an aliphatic or cycloaliphatic sulphonic acid having from 6 to 20 carbon atoms after removal of a —SO$_3$H group therefrom, or a salt-forming derivative thereof.

16. A process for the preparation of a pharmaceutical composition which comprises mixing desferrioxamine-B methanesulphonate with a water-soluble salt of a sulphonic acid of formula RSO$_3$H where R is as defined in claim 1.

* * * * *